(12) United States Patent
Sapiens et al.

(10) Patent No.: US 12,114,927 B2
(45) Date of Patent: Oct. 15, 2024

(54) METHODS AND APPARATUS FOR ADDRESSING PRESBYOPIA

(71) Applicant: EyeQue Inc., Newark, CA (US)

(72) Inventors: Noam Sapiens, Newark, CA (US); John Serri, Newark, CA (US)

(73) Assignee: EyeQue Inc., Newark, CA (US)

( * ) Notice: Subject to any disclaimer, the term of this patent is extended or adjusted under 35 U.S.C. 154(b) by 760 days.

(21) Appl. No.: 17/223,944

(22) Filed: Apr. 6, 2021

(65) Prior Publication Data

US 2022/0087522 A1     Mar. 24, 2022

Related U.S. Application Data

(63) Continuation-in-part of application No. 16/809,482, filed on Mar. 4, 2020, now Pat. No. 11,503,997, and a continuation-in-part of application No. 16/685,017, filed on Nov. 15, 2019, now Pat. No. 11,484,195, said application No. 16/809,482 is a continuation-in-part of application No. 16/276,302, filed on Feb. 14, 2019, now Pat. No. 10,588,507, said application No. 16/685,017 is a continuation-in-part of application No. 16/276,302, filed on Feb. 14, 2019, now Pat. No. 10,588,507, and a continuation-in-part of application No. 16/176,631, filed on Oct. 31, 2018, now Pat. No. 11,432,718, said application No. 16/276,302 is a continuation-in-part of application No. 15/491,577, filed on Apr. 19, 2017, now Pat. No. 9,844,962.

(60) Provisional application No. 63/005,962, filed on Apr. 6, 2020, provisional application No. 62/579,558, filed (Continued)

(51) Int. Cl.
*A61B 3/032* (2006.01)
*A61B 3/024* (2006.01)
*A61B 3/04* (2006.01)

(52) U.S. Cl.
CPC .............. *A61B 3/032* (2013.01); *A61B 3/024* (2013.01); *A61B 3/04* (2013.01); *A61B 2560/0487* (2013.01)

(58) Field of Classification Search
CPC ........... A61B 3/032; A61B 3/024; A61B 3/04; A61B 2560/0487; A61B 3/09
USPC ....................................................... 351/239
See application file for complete search history.

(56) References Cited

U.S. PATENT DOCUMENTS

2005/0280777 A1\* 12/2005 Dai ................... A61B 3/032
351/205
2006/0264916 A1\* 11/2006 Yee ................... A61F 9/00808
606/5

(Continued)

*Primary Examiner* — Mohammed A Hasan
(74) *Attorney, Agent, or Firm* — Steven A. Nielsen; NielsenPatents.com

(57) ABSTRACT

Various presbyopia measurement systems are presented. Solutions include a consumer friendly system using a consumer's smart phone to present a test image. The test image by be viewed through a first lens, second lens and optional added lens such that the image is perceived to be approximately eight inches to two feet away from the consumer's eye. In addition to a lens system that may be attached to a consumer's smart phone, the systems presented include a presbyopia kit that my comprise an eyeglass kit comprising near vision attachments, mid vision attachments, clip on lenses and Plano frames. Disclosed systems include the use of the use of both the eyeglass kit and lens system that attaches to the consumer's phone.

10 Claims, 7 Drawing Sheets

Related U.S. Application Data on Oct. 31, 2017, provisional application No. 62/409,276, filed on Oct. 17, 2016.

(56) References Cited

U.S. PATENT DOCUMENTS

| | | | |
|---|---|---|---|
| 2007/0002274 A1* | 1/2007 | Somani | A61F 2/16 351/159.75 |
| 2008/0106698 A1* | 5/2008 | Dai | A61B 3/0025 606/5 |

* cited by examiner

METHODS AND APPARATUS FOR ADDRESSING PRESBYOPIA

CROSS-REFERENCE TO RELATED APPLICATIONS

This utility application is a CIP or continuation in part of U.S. application Smart Phone Based Virtual Visual Charts for Measuring Visual Acuity filed on Oct. 31, 2018 application Ser. No. 16/176,631 which claims priority from application 62/579,558 filed on Oct. 31, 2017, the contents of which are incorporated by reference.

This utility application claims the benefit of and priority of U.S. application 63/005,962 filed on Apr. 6, 2020.

This utility application is a CIP of U.S. patent application Ser. No. 16/685,017, Automated Personal Vision Tracker, filed on filed on Nov. 15, 2019, which is a continuation in part of U.S. patent application Ser. No. 16/276,302 Optical Method to Assess the Refractive Properties of an Optical System filed on Feb. 14, 2019 which is now U.S. Pat. No. 10,488,507 which is a continuation in part of U.S. patent application Ser. No. 15/491,557 filed on Apr. 19, 2017, not U.S. Pat. No. 10,206,566 which claims priority for provisional patent application 62/409,276 filed on Oct. 17, 2016.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

Vision is arguably the most important of the senses. The human eye and its direct connection to the human brain is an extremely advanced optical system. Light from the environment goes through the eye optical train comprised of the cornea, the pupil, and the lens and focuses to create an image on the retina. As all optical systems, light propagation through the eye optics is subject to aberrations. The most common forms of aberrations in the eye are defocus and astigmatism. These low order aberrations are the cause of the most common refractive eye conditions myopia (near-sightedness) and hyperopia (farsightedness). Higher order aberrations are also present and can be described most conveniently by the Zernike polynomials. These usually have a lower effect on visual function. The eye, like any other organ in the human body, may suffer from various diseases and disorders, the most prominent today are: cataract, AMD, glaucoma, diabetic retinopathy, dry eye. Other conditions exist and should also be considered in the scope of this application.

Ophthalmic measurements are critical for eye health and proper vision. Those ophthalmic measurements could be sectioned into objective and subjective types. Objective types measurements give a metric of a physiological, physical (e.g. mechanical or optical), biological or functional without the need for input from the measured individual (patient, subject, user or consumer). Examples of objective tests include but are not limited to OCT (optical coherent tomography used to image a 3 dimensional and cross sections of the eye), scanning laser ophthalmoscope (SLO, used for spectral imaging of the retina), fundus image (used to present an image of the retina), auto-refractor (used for refraction measurement), keratometer (used for providing a profile of the cornea), tonometer (used to measure the IOP—intra ocular pressure). Subjective measurements give a metric with relation to the individual input. That is, they provide parameters that also take into consideration the brain functions, perception and cognitive abilities of the individual. Examples of subjective tests include but are not limited to visual acuity test, contrast sensitivity test, phoropter refraction test, color vision test, visual field test, and the EyeQue PVT and Insight.

Today, both objective and subjective eye exams (measurements) are done by an ophthalmologist or an optometrist. The process usually involves the patient needing to schedule an appointment, wait for the appointment, travel to the appointment location (e.g. office or clinic), wait in line, perform multiple tests using various tools and potentially moving between different technicians and different eye doctors. The prolonged wait times both for the appointment as well as in line at the appointment location, along with the hassle of performing the tests with different professionals and the duration of those tests might seem daunting to many patients. Furthermore, the shear effort associated with the process and even the requirement of remembering to start the process to begin with might deter patients from going through with it.

Moreover, currently about 2.5 billion people do not have access to eye and vision care at all. The cost of eye exams could be considered quite significant especially in some places in the world. This poses a hindrance to the availability of eye care in third world countries for example. The cost, time consumption and perceived hassle also makes it at times prohibitive to have repeated eye exams, especially at the desired frequency. Those might be necessary in special cases (for example after refractive surgery or cataract surgery where repeated measurements should be performed to track the progress of the patient's status over time and the success of the surgery. Additionally, even under normal circumstances, measurements at a doctor's office only represent a single point in time. The situation under which the measurements were made might not be optimal or do not fully represent the patient's characteristics. The patient might have been tired, stressed or agitated (a doctor's visit might be quite stressful in and of itself but could also being run from test to test and being posed with questions and options elevate the patient's level of stress) or was just in a bad mood. Even the state of mind of the doctor themselves might influence the way the measurement is performed. Beyond all that, the time of day and other environmental conditions (whether direct e.g. lighting conditions or indirect e.g. temperature) could also affect the measurement and provide incomplete or false information.

The availability of information (including specifically medical information) on the internet, the increased awareness of people for preventive medicine, and the emergence of tele-medicine leads to many taking control of their own health. Devices for screening, monitoring and tracking medical conditions are quite pervasive in today's world, for example blood pressure measurement devices, and blood sugar monitors. The technological advancements allow for people to be more independent in diagnosis, prevention and tracking of various health conditions. Furthermore, many prefer to perform these activities in the comfort of their homes without the need for appointments or other time-consuming activities. In case of an anomaly, they would call or email their physicians to consult for the appropriate course of action.

The advancement of technologies effectively makes computers with screens and cameras ubiquitous in the form of laptops, tablets and smartphones. Therefore, enabling many people to have a device already capable of computing displaying and recording information.

All this brings the need for a series of devices that will enable users to perform ophthalmic measurements at home, by themselves, in a timely and cost-effective manner. It should be clear that the quality of these measurements and their accuracy and precision should meet or exceed the standards of today's measurement methods.

This vision could be further enhanced by use of cloud-based data and analytics that enables complete access to the entire history of a patient exams, tests and measurements. Moreover, the use of artificial intelligence (AI) will enable diagnosis based on machine learning and big data. This could be done by means of data mining, neural network decision making and pattern detection and recognition, as some examples of the AI capabilities.

To summarize, the vision for eye care in the not so far future will look like: A complete solution for eye and vision care for consumers and doctors; Remote, self-administered battery of tests for both disease and functional; measurements are enabled by technology and devices, AI is used for analysis, tracking and reporting. Enhanced by big data correlations and insights.

In simple terms, as an example: A person sits on their couch at the comfort of their home, uses a device to do various measurements, that data is uploaded to an AI for analysis. The AI will let the person know the results and notify the doctor. The AI will initiate alerts for the person and doctor in necessary cases. The person will not need to get up unless a serious issue occurs (i.e. surgery). All other issues will be dealt with remotely (e.g. email/phone/video conference with the doctor, order glasses and have them delivered to the home, direct delivery of doctor prescribed medications).

Despite the apparent approach of "direct to consumer", the methodologies could easily be implemented for a more enterprise like model. One example of such implementation will have a hierarchical structure in which an entity such as a hospital, association, or a medical insurance company provides the ability for the doctors to provide their patients with such devices and capabilities. The devices are all connected through the user accounts to the cloud and the measurements are streamed directly into the users' accounts (and potentially their medical records). Those accounts could be attached to one or more doctors and can also be transferred and shared.

FIELD OF THE INVENTION

The invention generally relates to the measurement and solution of presbyopia. As a person ages, their ability to accommodate diminishes. In other words, their ability to change their focus by changing the shape of their lens is reduced. This condition is called presbyopia and it occurs gradually, usually by the age of 45. The most prevalent solution is reading glasses. Bi-focals, tri-focals and progressive lenses are also available to provide a solution to far and near vision in the same set of corrective eyewear. In most cases, the measurement of correction needed in reading glasses is self administered in a process of a trial and error. In other words, a person goes to a store and tries on different glasses until they can read a piece of text presented in front of them. This is done even in convenience stores with a stand of glasses and a paragraph of text presented to the customers. These glasses are usually standard in their number and are identical in terms of binocularity (right eye and left eye numbers are the same). Alternatively, eye doctors prescribe a near vision add (NVADD) to a prescription set of glasses based on the person's far vision prescription and their age. These NVADD numbers are also usually identical binocularly. In some cases a small Snellen or ETDRS chart, made specifically for near vision is presented to the user for measuring the near vision add required. The measurement that uses the charts follows the same optical procedures as a standard eye exam for far vision glasses.

DESCRIPTION OF THE RELATED ART

The known related art fails to anticipate or disclose the principles of the present invention.

In the related art, there is no real measurement of a person's near vision at most cases. Furthermore, when a measurement is done it is not accurate as it relies on the measurement distance controlled by the user.

In a somewhat related field, measurement of mid-vision is seldom done. The requirement for mid-vision distances relates to the increasing use of computers and other devices that require reading or other vision capabilities in distances that are neither far nor near.

Thus, there is a long felt need in the art for the present invention.

BRIEF SUMMARY OF THE INVENTION

The present invention overcomes shortfalls in the related art by presenting an unobvious and unique combination and configuration of methods and components to measure and solve presbyopia for a user.

The invention overcomes shortfalls in the related art by using an optical device for measuring the user's presbyopia. In addition, a solution for the presbyopia may be presented followed by the person's vision remeasured to verify the solution validity and efficacy.

Embodiments of the invention may include the use of an optical system that projects an image onto a user's retina as if that image originated at a near distance. In an embodiment of the invention, the optical system may include a smartphone as a source of light and images. In another embodiment of the invention, the optical system may be adjusted from a far vision measurement device to a near vision measurement device. In yet another embodiment, a mid range vision measurement may be conducted.

The invention could be implemented as an addition to an existing measurement system that measures the far vision of a user. The addition could be in the form of an insert, an add-on or an attachment for example. Another implementation could include moving one of the lenses to allow for the image plane to be shifted to the near and mid rage distances.

In one disclosed process, a user will use the measurement device to measure their near vision. They will then iterate on near vision correction glasses or clip-ons for example, taking repeated near vision measurements until they achieve acute near vision.

These and other objects and advantages will be made apparent when considering the following detailed specification when taken in conjunction with the drawings.

Figure 1:
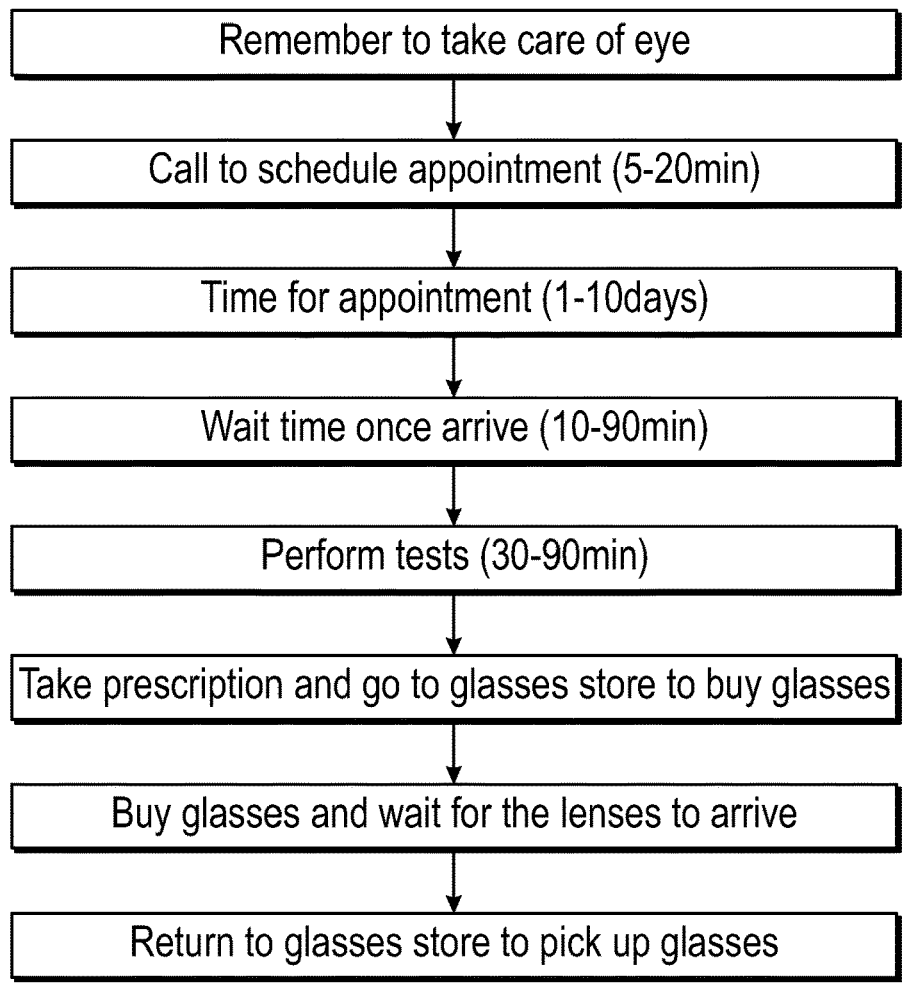
FIG. 1 Current process for obtaining eye glasses
Figure 2:
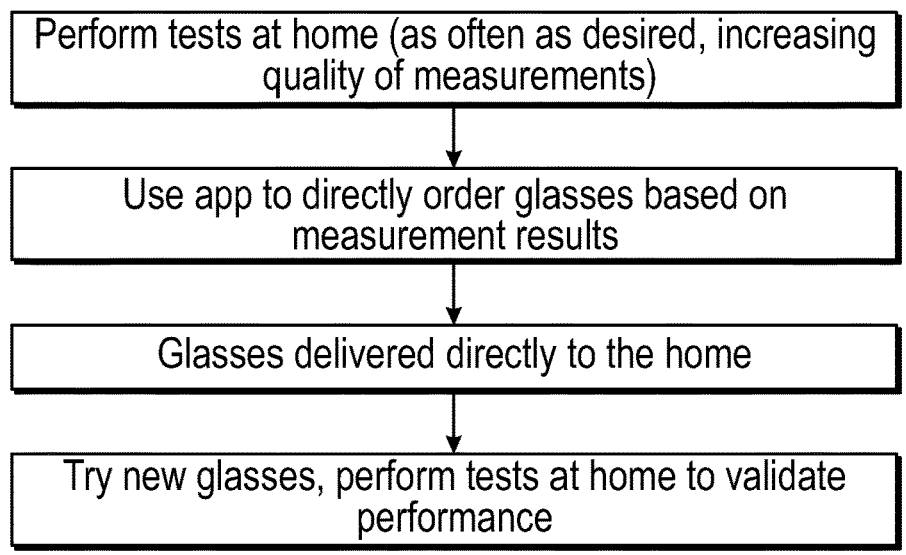
FIG. 2 Proposed example of process for obtaining eyeglasses
Figure 3:
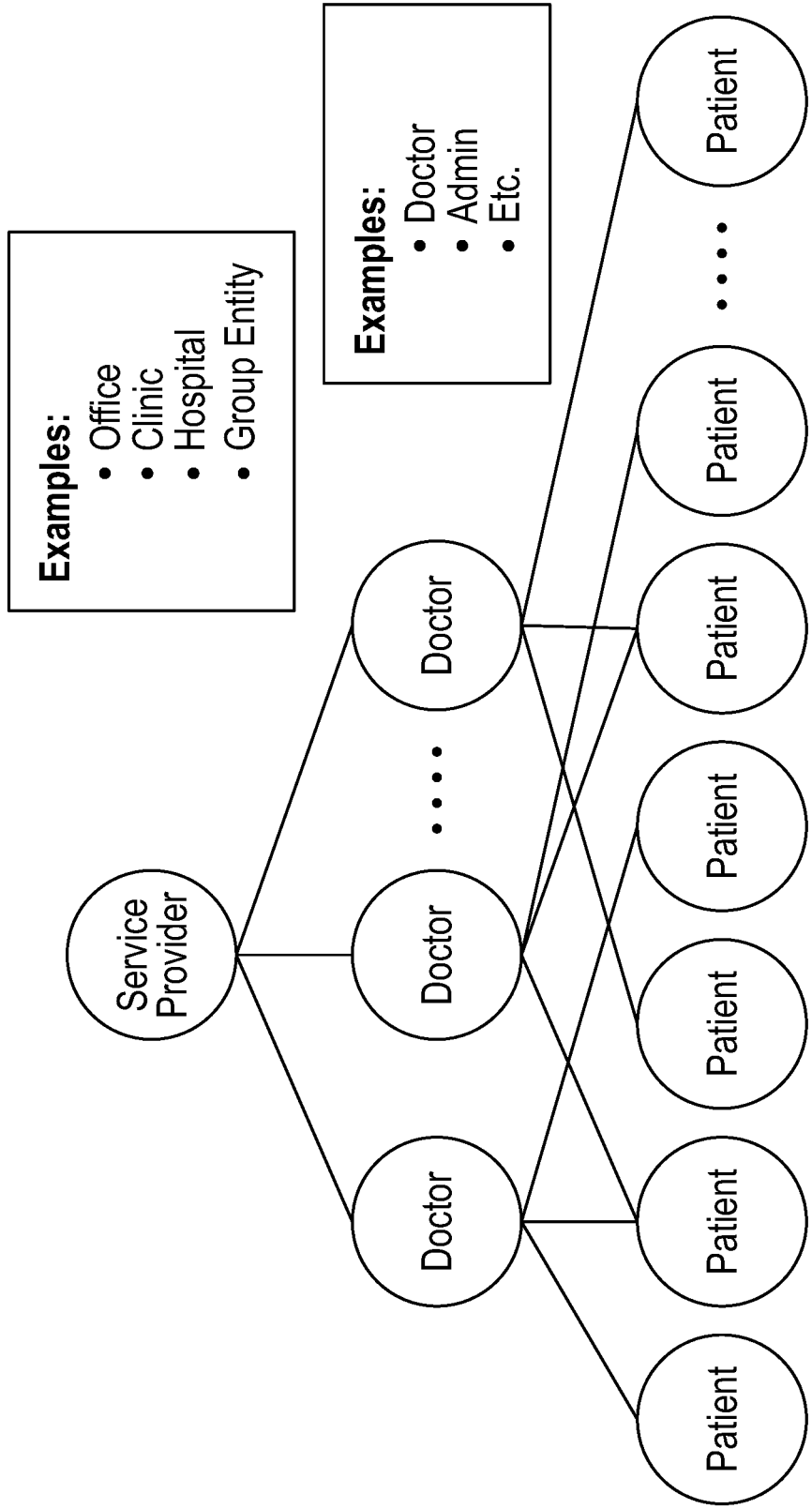
FIG. 3 Example of proposed enterprise model

REFERENCE NUMERALS IN THE DRAWINGS 100 a disclosed a presbyopia measurement device
120 a disclosed multi distance measurement device
320 a first lens
320A a first lens in a first position
320B a range of positional adjustments by a first lens
320C a first lens in a second position
325 a first surface or front surface comprising an aspherical surface of a first lens 320
330 a second surface or back surface comprising a concave surface of a first lens 320
360 a second lens or spherical convex lens
380 distal or fare eye point of sight rays
405 display or screen surface of smartphone or other device
600 an eye or other optical measurement system
900 added lens or a proposed presbyopia attachment to an existing far vision measurement device, added to the front of the device
920 added lens to the back of an existing vision measurement device
950 near vision attachment or lens, may be attached to eyeglass lens
960 mid vision attachment or lens, may be attached to eyeglass lens
970 clip on lenses, may be attached to existing eyeglasses for far or mid range vision
980 Plano frames
1000 a proposed

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

Figure 4:
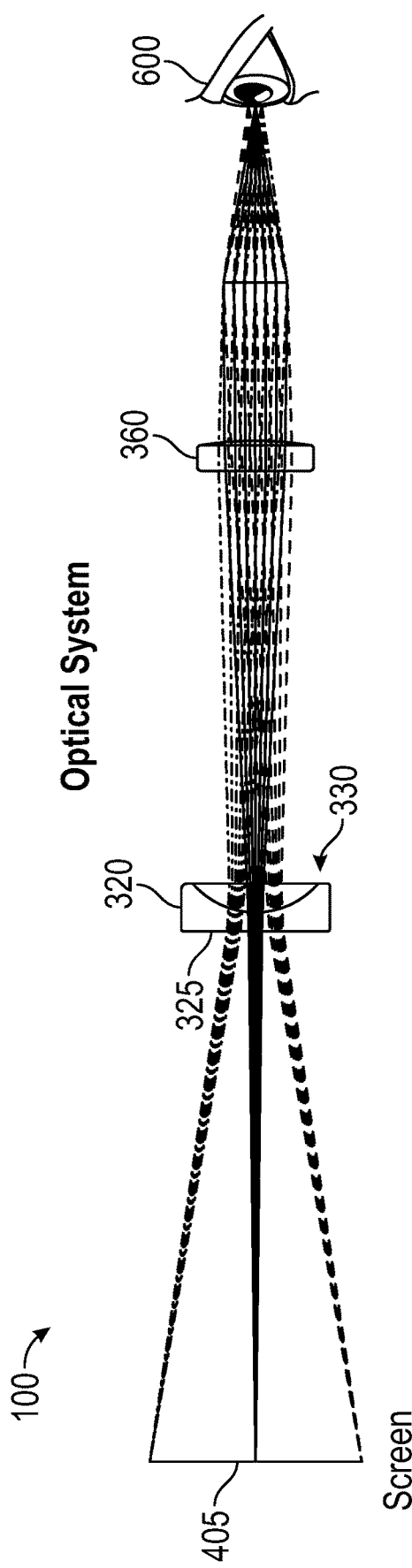
FIG. 4 Example of a proposed presbyopia measurement device

In an embodiment of the invention a measurement device (FIG. 4) is designed to present images to the user such that those images appear to originate at a distance corresponding to reading distance, for example 1 ft away. In this embodiment of the invention light from a screen, smartphone, tablet or other device capable of projecting images goes through a first optical element and a second optical element, for example lenses. This system provides a capability to gather light from the screen such that the resolution of the screen is sufficient to produce an image onto a user's retina with enough detail to allow for the measurement of the user's visual acuity down to at least 20/20 on the Snellen chart for example. The system also is built to generate beams of light into the user's pupils as though they arrive from an object placed at a near distance from the user. The system could then be used to measure the user's near visual acuity for example. Other measurements could be included such as contrast sensitivity. The system could also be built to make the beams appear to arrive from an object located at mid-range vision distances (e.g. 2 ft away) to allow for measurements of the visual acuity or other parameters of the user's vision for that distance.

Figure 5:
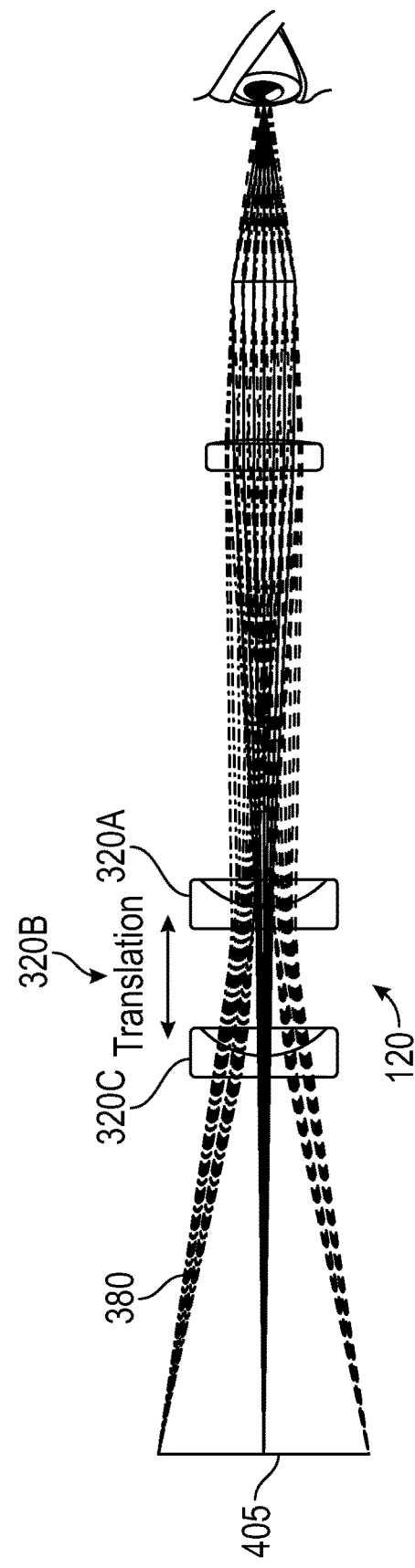
FIG. 5 Example of a multi distance measurement device

In another embodiment of the invention presented in FIG. 5, the system could be built to accommodate for different distances. The optical system could be built with one of the optical elements placed on a translation stage. Moving the optical element along the optical axis will cause the beams arriving at the user's pupil to appear to be coming from different distances (for example, from infinity down to 1 ft). Alternatively, multiple lenses may be placed in a barrel, wheel or slide, each at different distances such that changing between the lenses will introduce different apparent distances to the user. In an example of an implementation of the proposed embodiment, there will be three lenses placed at different distances on a mechanism to replace between the lenses. The lenses could correspond to far vision, near vision and mid-vision apparent distances, for example. In yet another example of an implementation of the embodiment of the invention, a tunable lens (liquid, rubber or other) could be placed instead or in addition to the first or second lens to control the distance a user will be observing. Another advantage of the use of a tunable lens would be to allow a user to introduce different corrections in addition to the introduced optical change performed for the different distances.

Figure 6:
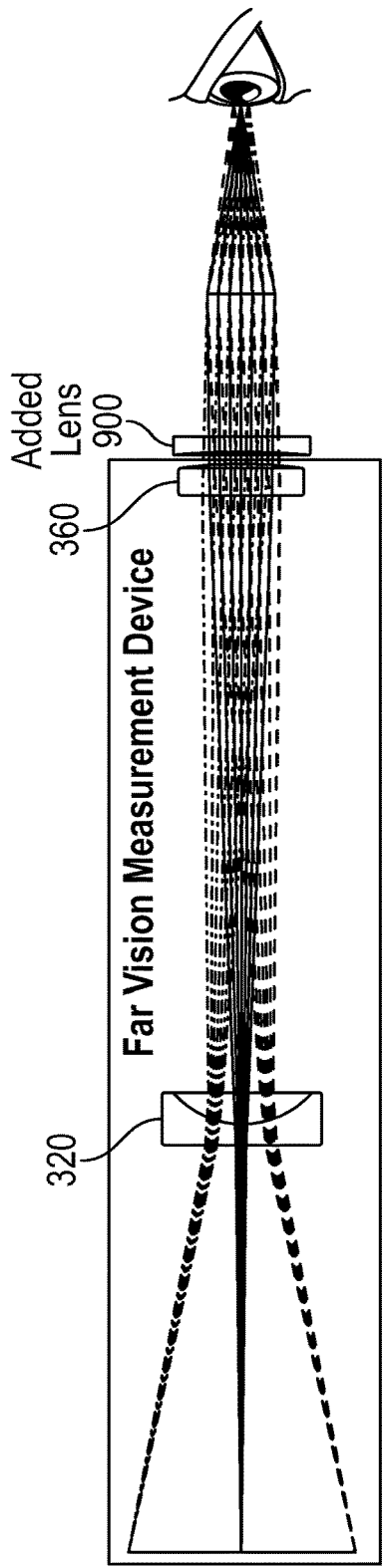
FIG. 6 Example of a proposed presbyopia attachment to an existing far vision measurement device—front of device FIG. 7 Example of a proposed presbyopia attachment to an existing far vision measurement device—back of device FIG. 8A perspective view of a proposed presbyopia near vision attachment FIG. 8B perspective view of a proposed mid vision presbyopia attachment FIG. 9 Example of a proposed presbyopia solution kit FIG. 10 Example of a proposed presbyopia measurement process
Figure 7:
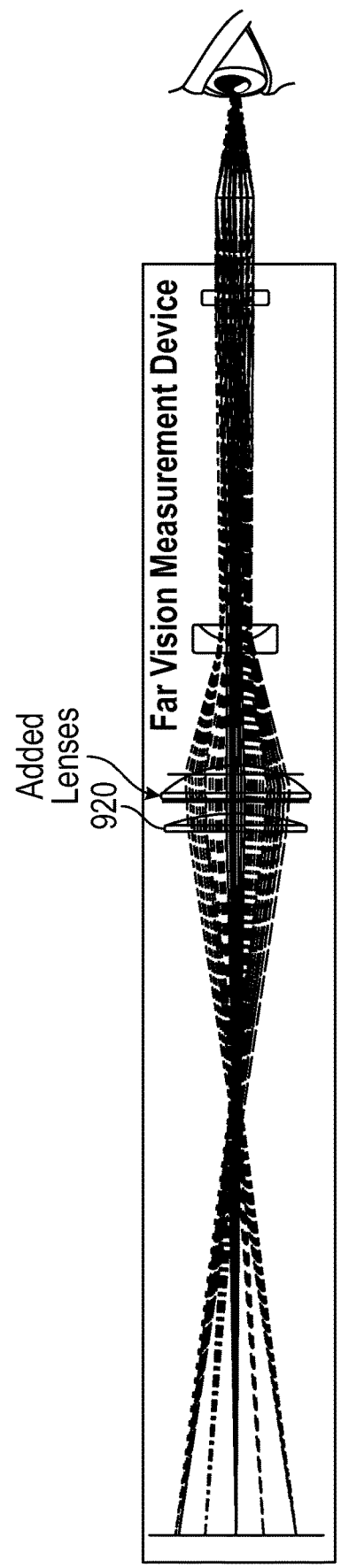

In yet another embodiment of the invention, an insert or attachment for example may be used to convert a far vision measurement device as exemplified in cross referenced patent application Ser. No. 16/176,631 to a near vision or mid-vision measurement device. This could be done by presenting an additional element, e.g. a lens either at the end of the device that is closest to the user (FIG. 6) or to that closest to the screen (FIG. 7). An example of a lens attached to the front of the device would be a −3.25 D lens to introduce a near vision distance of 1 ft image from the user. The attachment of the optical element to the end closest to the user introduces simplicity but has the disadvantage in the device presented in cross referenced patent application Ser. No. 16/176,631 is the fact that the added optical element is not translated according to the user's pupillary distance. This problem could be mitigated by optical design to an acceptable extent. The use of meniscus lenses would reduce the introduction of prism due to the offset of the lenses from the optical axes defined by the user's pupillary distance. Alternatively, the attachment of the lenses onto the part of the device that moves according to the user's PD will also solve the PD dependence. The attachment of the optical element in the side closest to the screen introduces much chromatic aberrations. This problem could be solved by introduction of a compound achromatic lenses.

Figure 8B:
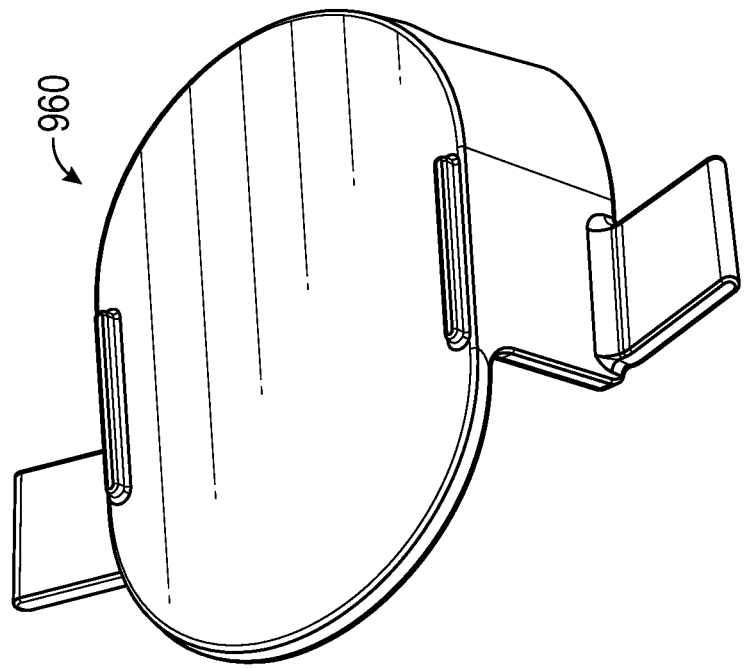
Figure 8A:
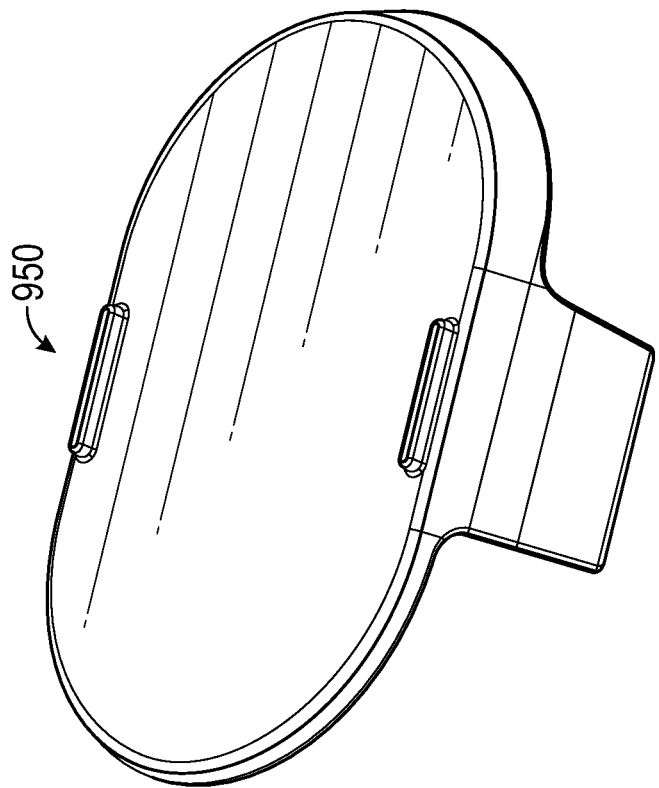

In an implementation of the proposed embodiment of the invention, an attachment is placed on the front part of the far vision measurement device. The attachment is comprised of a lens and a mechanical implement (FIG. 8) that attaches the lens to the output window of the far vision measurement device. The attachment lens makes the image appear as if it arrives from a near or mid-vision ranges, depending on the lens used.

Figure 9:
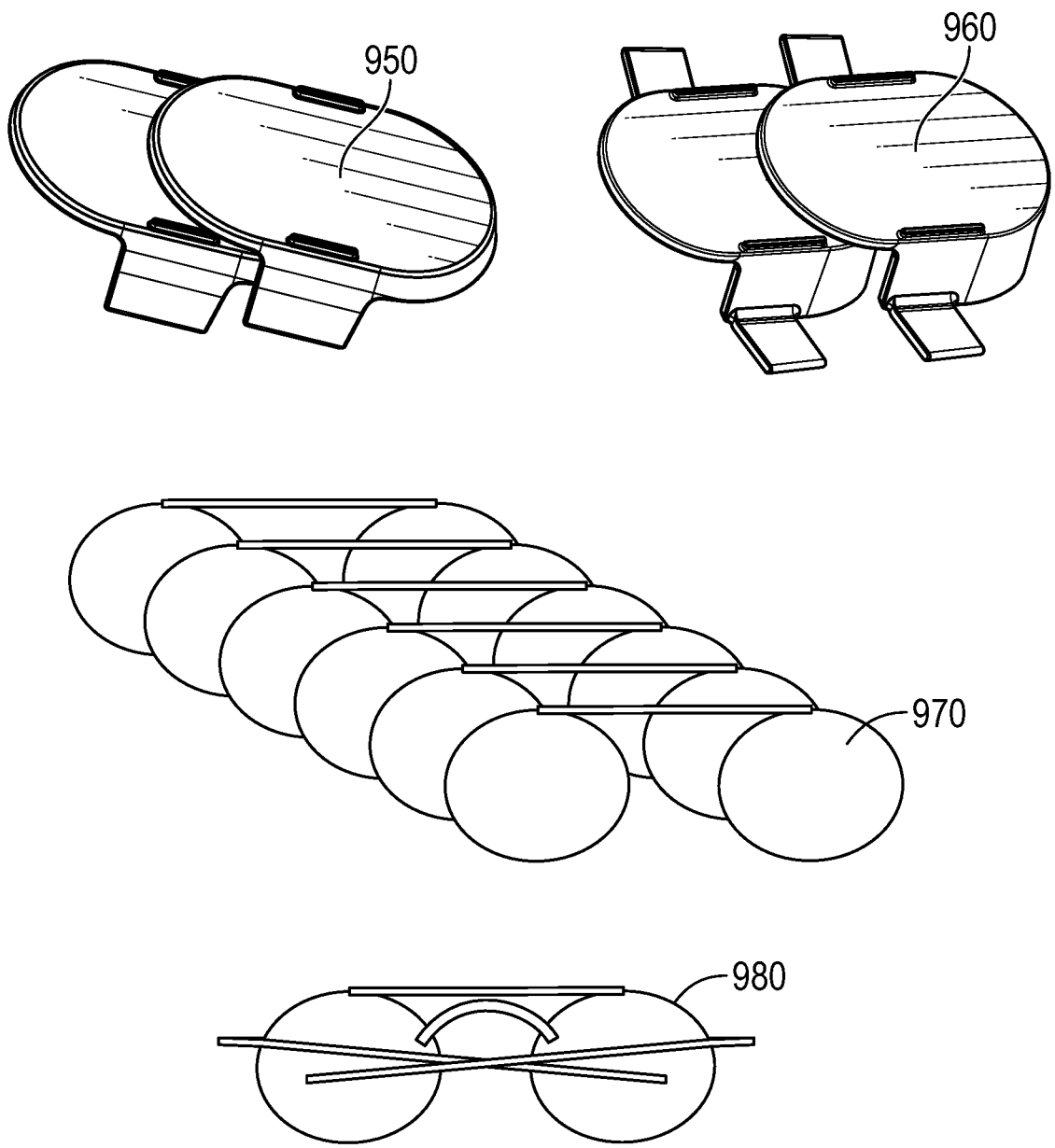

In an embodiment of the invention, a presbyopia solution is presented (FIG. 9). The solution is comprised of a far measurement device that could also be separate from the solution itself. In addition, near and mid vision attachment are included as well as a pair of plano frames and asset of powered clip-ons (FIG. 9). This presbyopia solution including the far measurement device and the presbyopia kit allows the user to determine which power they require for correction for both near and mid vision distances. The plano frames are used in case a user does not have any correction for far vision. If the user has far vision correction, they should be using their single vision glasses for the measurement and the determination of their near vision and mid-vision adds. An alternative could be using the plano frame while wearing far vision correction contact lenses. The clip-ons are powered lenses that can be externally attached to a glasses frame. The clip-ons include a pair of lenses of specific power and a mechanical contraption for attaching the lenses to a glasses frame. The kit should include a set of clip-ons with different powers, for example from +1 D to +3.5 D in 0.5 D increment (6 pairs).

Figure 10:
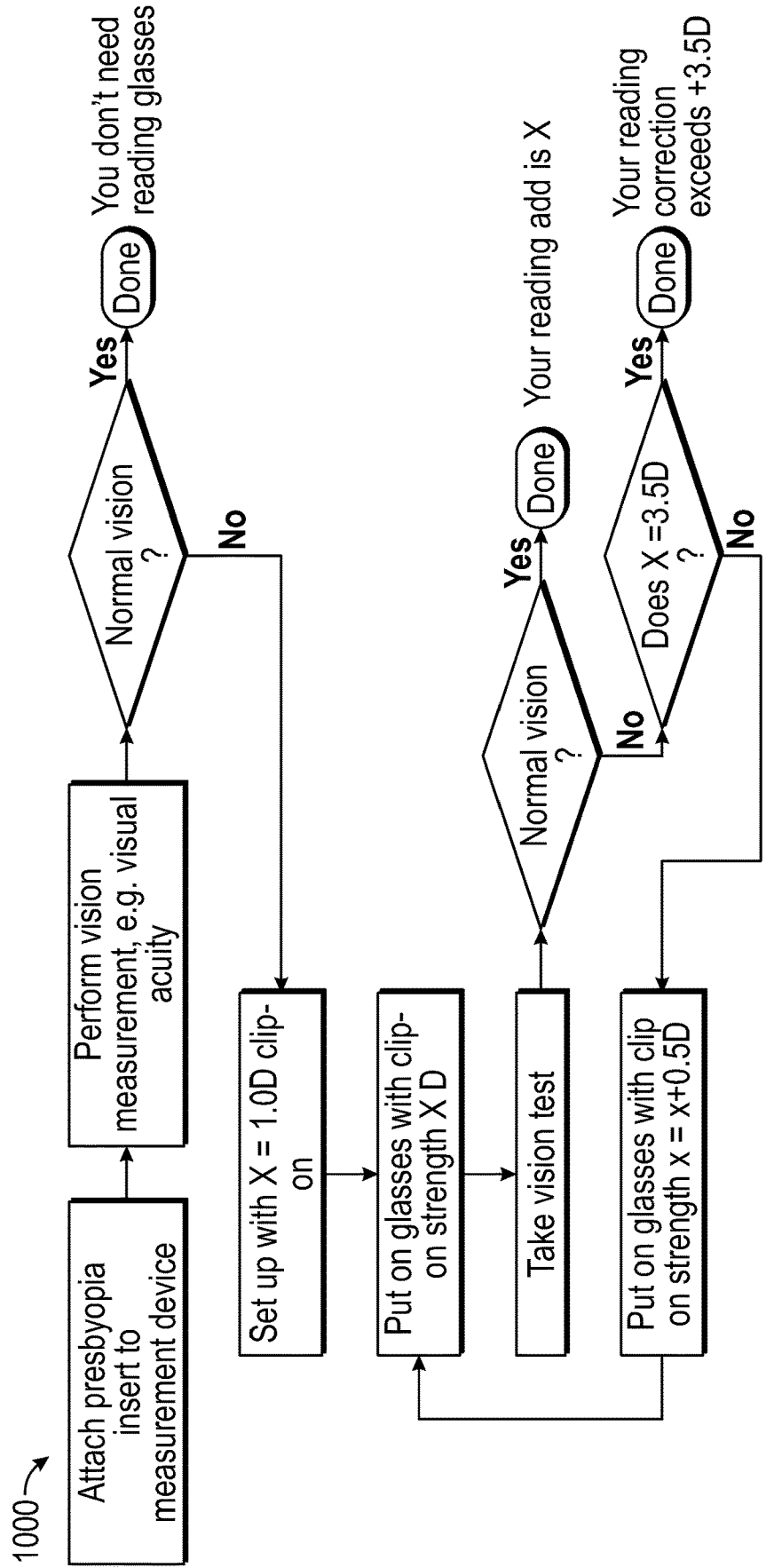

In an embodiment of the invention, a process for the use of a presbyopia solution is presented (FIG. 10). The process includes a first step of attaching a presbyopia insert to a measurement device. The measurement device could be for example a far vision measurement device and the attachment could be for example a near vision or a mid-vision lens. The process continues to make a vision measurement, for example a visual acuity test (e.g. ETDRS or Snellen). If the user's result is normal vision then the test is complete and the user is notified they do not need near vision or reading glasses, or mid-vision glasses (corresponding to the used attachment). In case the result is not normal vision, the user is instructed to use the provided plano frame in case they have normal far vision or use contact lenses to correct their far vision. They are also, instructed to use the clip-on with the +1 D power. The user is then instructed to repeat the vision test. If the result indicates normal vision, the power of the clip-on is reported as the near or mid-vision add/number for the user. If the results are not of normal vision, the user repeats the process for incremental increase of the optical power of the clip-ons until normal vision is achieved or the limit of the clip-on optical power is achieved. In case the results still do not indicate normal vision with the maximum power, the user is provided with an explanation to that fact. The test could be done for each eye individually, thus providing customized near and mid-vision adds/numbers to the user.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Items

Disclosed embodiments may include the following items:

1. A method of measuring presbyopia (FIG. 4), the method comprising the steps of:
   a) using a series of lenses to present images to a user such that the images have optical qualities of an image presented in the range of 10 inches to 2 feet.
2. The method of 1, further comprising the steps of using a first lens (320) the first lens comprising a front surface comprising an aspherical surface (325) and the first lens comprising back concave surface (330).
3. The method of 2 further comprising the use of a second lens (360) the second lens being a spherical convex lens disposed proximal to an optical system such as an eye (600).
4. The method of 3 further including the step of using a screen image (405) proximal to the first lens, the screen image passing through the first lens, second lens and to the measured optical system (600).
5. The method of 4 further including the step of moving the first lens along an optical axis to present multiple perceived image distances to the measured optical system.
6. The method of 5 further including a first position (320A) and a second position (320C) for the first lens, with the first lens moving along an optical axis (320B).
7. The method of 6 using an added lens (900) disposed between the second lens and the optical system being measured, the added lens used to adjust the perceived distance between the screen image from the optical system being measured.
8. The method of 6 wherein the added lens (920) is disposed between the first lens and screen image.
9. The method of 7 wherein the added lens comprising a plurality of lenses.
10. The method of 8 wherein the added lens comprises a plurality of added lenses that are used for measurement of far vision, near vision and mid-vision testing.
11. The method of 8 wherein the added lens comprises a turnable lens.
12. A method for measuring presbyopia (FIG. 9) the method comprising the steps of:
    a) using plano frames, a plurality of clip on lenses, a pair of near vision attachments and a pair of mid vision attachments.

What is claimed is:

1. A method of measuring presbyopia, the method comprising the steps of:
   a) using a series of lenses to present images to a user such that the images have optical qualities of an image presented in the range of 10 inches to 2 feet;
   b) of using a first lens the first lens comprising a front surface comprising an aspherical surface and the first lens comprising back concave surface.

2. The method of claim 1 further comprising the use of a second lens the second lens being a spherical convex lens disposed proximal to an optical system such as an eye.

3. The method of claim 2 further including the step of using a screen image proximal to the first lens, the screen image passing through the first lens, second lens and to the measured optical system.

4. The method of claim 3 further including the step of moving the first lens along an optical axis to present multiple perceived image distances to the measured optical system.

5. The method of claim 4 further including a first position and a second position for the first lens, with the first lens moving along an optical axis.

6. The method of claim 5 using an added lens disposed between the second lens and the optical system being measured, the added lens used to adjust the perceived distance between the screen image from the optical system being measured.

7. The method of claim 6 wherein the added lens comprising a plurality of lenses.

8. The method of claim 5 wherein the added lens is disposed between the first lens and screen image.

9. The method of claim 8 wherein the added lens comprises a plurality of added lenses that are used for measurement of far vision, near vision and mid-vision testing.

10. The method of claim 8 wherein the added lens comprises a turnable lens.

* * * * *